United States Patent
Lubatschowski (10) Patent No.: US 11,406,535 B2
(45) Date of Patent: Aug. 9, 2022

(54) DEVICE FOR CREATING AN APERTURE IN THE EYE

(71) Applicant: ROWIAK GMBH, Hannover (DE)

(72) Inventor: Holger Lubatschowski, Hannover (DE)

(73) Assignee: ROWIAK GMBH, Hannover (DE)

( * ) Notice: Subject to any disclaimer, the term of this patent is extended or adjusted under 35 U.S.C. 154(b) by 0 days.

(21) Appl. No.: 16/760,694

(22) PCT Filed: Oct. 30, 2018

(86) PCT No.: PCT/EP2018/079677
§ 371 (c)(1),
(2) Date: Apr. 30, 2020

(87) PCT Pub. No.: WO2019/086436
PCT Pub. Date: May 9, 2019

(65) Prior Publication Data
US 2020/0330277 A1   Oct. 22, 2020

(30) Foreign Application Priority Data

Oct. 30, 2017  (DE) .......................... 102017125422.6

(51) Int. Cl.
*A61F 9/008*   (2006.01)
(52) U.S. Cl.
CPC ........ *A61F 9/00827* (2013.01); *A61F 9/0084* (2013.01); *A61F 2009/00895* (2013.01)
(58) Field of Classification Search
CPC ............... A61F 9/00827; A61F 9/0084; A61F 9/00838; A61F 2009/00895; A61F 2009/0087; A61F 2009/00897
See application file for complete search history.

(56) References Cited

U.S. PATENT DOCUMENTS

| | | |
|---|---|---|
| 4,955,904 A | 9/1990 | Atebara et al. |
| 5,757,458 A | 5/1998 | Miller et al. |
| | (Continued) | |

FOREIGN PATENT DOCUMENTS

| | | |
|---|---|---|
| EP | 2231084 | 9/2010 |
| EP | 2468226 | 6/2012 |
| | (Continued) | |

OTHER PUBLICATIONS

Alio, Jorge L., et al., "Removability of a small aperture intracorneal inlay for presbyopia correction," Journal of refractive surgery 29 (8), pp. 550-556 (2013).

*Primary Examiner* — Mallika D Fairchild
*Assistant Examiner* — Shreya Anjaria
(74) *Attorney, Agent, or Firm* — Price Heneveld LLP (57) ABSTRACT

The present invention relates to the field of devices for correcting or mitigating refractive errors in the eye, more particularly, to a solution in which desired improvements in eyesight are achieved as far as possible without limiting everyday activities and where performing the treatment itself involves minimum risk by use of a device for creating an aperture in an eye, the device having a control unit for a laser unit, and the control unit is designed to control the laser unit to create the aperture in a lens of the eye, wherein the aperture is used to increase the depth of field of the eye and is formed by laser-induced lesions which reduce light transmission through a lens aperture region surrounding an aperture opening.

20 Claims, 9 Drawing Sheets

(56) References Cited

U.S. PATENT DOCUMENTS

| | | | |
|---|---|---|---|
| 5,980,040 A | 11/1999 | Xu et al. | |
| 5,993,438 A * | 11/1999 | Juhasz | A61F 9/008 606/10 |
| 2004/0199149 A1 | 10/2004 | Myers | |
| 2006/0095023 A1* | 5/2006 | Loesel | A61F 9/00825 606/5 |
| 2010/0004641 A1* | 1/2010 | Frey | A61F 9/00827 606/4 |
| 2012/0172852 A1* | 7/2012 | Lubatschowski | A61F 9/00838 606/4 |
| 2013/0131795 A1 | 5/2013 | Miller et al. | |
| 2015/0141972 A1* | 5/2015 | Woodley | A61F 9/0084 606/5 |
| 2019/0167478 A1* | 6/2019 | Sunalp | A61F 9/008 |

FOREIGN PATENT DOCUMENTS

| | | | |
|---|---|---|---|
| WO | 2011020078 | 2/2011 | |
| WO | WO-2011020078 A1 * | 2/2011 | A61F 2/1659 |

* cited by examiner

DEVICE FOR CREATING AN APERTURE IN THE EYE

CROSS-REFERENCE TO FOREIGN PRIORITY APPLICATION

The present application claims the benefit under 35 U.S.C. §§ 119 (b), 119(e), 120, and/or 365 (c) of PCT/EP2018/079677 filed Oct. 30, 2018, which claims priority to German Application No. 102017125422.6 filed Oct. 30, 2017.

FIELD OF THE INVENTION

The present invention relates to the field of devices for correcting or mitigating refractive errors in the eye, and, in particular, to a device for creating an aperture in an eye, with which the depth of field of the eye is increased, which may result in improved eyesight particularly in cases of farsightedness due to age (presbyopia).

BACKGROUND OF THE INVENTION

A refractive error of the eye is generally remedied by spectacles or contact lenses. In cases of ametropia, an object at optical infinity is not imaged sharply on the retina when the ciliary muscle is relaxed (near approximation). When the eyeball is too long in comparison with the total refractive power of the cornea and lens, this is referred to as myopia (near-sightedness or short-sightedness). Glasses or contact lenses that act as a diverging lens can reduce the refractive power so that a sharp image is formed on the retina. In the converse case of hyperopia (long-sightedness), the refractive power of the eye media is too small in relation to the eyeball length. In this case, a converging lens in the form of glasses or a contact lens can correct the refractive error. If the refractive error is in one plane only, this is referred to as astigmatism. Appropriate cylindrical lenses, likewise in the form of glasses or contact lenses, can correct this refractive error.

In addition to glasses or contact lenses as corrective aids, there are surgical procedures for correcting refractive errors of the eye.

Parts of the cornea can be removed using lasers, thus modifying the anterior curvature of the cornea in such a way that the optical refractive power of the eye is changed accordingly, and (approximately) normal vision (emmetropia) is achieved. One advantage of such laser procedures (PRK: photorefractive keratectomy, LASIK: laser-assisted in-situ keratomileusis, LASEK: Laser epithelial keratomileusis) derives from the flexibility of the correction to be achieved. Corneal irregularities can be corrected in a targeted manner, which is often not possible with glasses and contact lenses.

It is also possible to insert implants into the cornea, the aim of which is to correct the specific refractive error by means of their optical refractive power or their biomechanical effect (for example, by modifying the curvature of the cornea). Intraocular lenses can also be implanted into the eye to correct refractive errors. These can act in addition to the natural lens of the eye, or replace the natural lens of the eye.

Implant solutions also include a group of implants which make use of the principle of the stenopeic hole (pinhole effect). The aperture reduces interfering marginal rays, thus reducing spherical aberrations in imaging. The circles of confusion on the retina are made smaller, thus increasing the depth of field in imaging. Ametropic eyes consequently acquire greater visual acuity when looking through a pinhole aperture.

In one variant of such an approach, a plastic disc approximately 5 µm thick, with an open internal diameter of approximately 1.6 mm and an external diameter of 3.8 mm is centrally inserted into the cornea of the eye. This is mostly done operatively by using a laser to create a pocket in the cornea, into which the implant is fixated.

In another variant, an artificial intraocular lens (IOL) is implanted into the eye. The natural lens is removed in the process. Inside the artificial lens, there is likewise a pinhole aperture with an open internal diameter of approximately 1.36 mm and an external diameter of 3.23 mm.

Finally, the pinhole effect can also be utilised with the aid of a contact lens. However, contact lenses can generally move easily on the cornea. The central opening is moved out of the visual axis, thus impairing optimal vision.

Examples from the prior art which relate to utilisation of the pinhole effect can be found, for example, in U.S. Pat. Nos. 4,955,904, 5,757,458, 5,980,040, WO 2011/020078 A1 and US 2013/131795 A1.

In everyday life, glasses can be damaged or lost. Depending on the surroundings, they can become dirty or can mist up. Irregular refractive errors, other than myopia, hyperopia, or astigmatism can be corrected only to an inadequate extent or not at all, and this is also the case with contact lenses, which additionally require a certain amount of dexterity when inserting and removing them.

Surgical procedures using laser and implants involve risks of infection during and after the operation and/or of tissue intolerance to the implant. Inserting the pinhole implant in the cornea is known to have adverse effects on the supply of nutrients to the tissue (Alio, Jorge L.; et al. (2013): Removability of a small aperture intracorneal inlay for presbyopia correction. in: Journal of refractive surgery 29 (8), pp. 550-556).

One object of the present invention is to restore reading ability to presbyopic eyes. An additional or further object is to correct visual defects caused by aberrations, in particular, in the periphery of the optical axis of the eye, the aim being to mask the marginal rays of the light entering the eye. The disadvantages of the prior art are to be avoided completely or at least substantially thereby.

SUMMARY OF THE INVENTION

It is, therefore, desirable to present a solution in which the desired eyesight improvements are achieved as far as possible without limiting everyday activities, and where performing the treatment itself involves minimum risk.

According to a first aspect of the invention, a device for creating an aperture in an eye is proposed, said device having a control unit for a laser unit, the control unit being designed to control the laser unit to create the aperture in a lens of the eye, wherein the aperture is used to increase the depth of field of the eye and is formed by laser-induced lesions which reduce light transmission through a lens aperture region surrounding an aperture opening.

Other aspects of the invention include a method of generating control commands for a laser unit for creating an aperture in an eye, wherein the control commands cause the laser unit to create the aperture in a lens of the eye, wherein the aperture is used to increase the depth of field of the eye and is formed by laser-induced lesions which reduce light transmission through a lens aperture region surrounding an aperture opening, and a method of creating an aperture in an eye, said method comprising the step of controlling a laser unit to create the aperture in a lens of the eye, wherein the aperture is used to increase the depth of field of the eye and is formed by laser-induced lesions which reduce light transmission through a lens aperture region surrounding an aperture opening.

As the (pinhole) aperture is created in the eye itself, the problems discussed in connection with external aids such as glasses or contact lenses do not occur. The aperture is not surgically implanted either, so there is no significant risk of infection or intolerance. As the invention allows the aperture to be attached non-invasively, a sterile environment (operating theatre) is not required. Nor is it specified that substances (dyes, pigments) be introduced into the eye, so no intolerances are to be feared in that respect, either.

In contrast to the prior art, the present invention offers the advantage that an aperture can be inserted into the lens of the eye non-invasively, i.e., without surgically opening the eye. The aperture masks marginal rays, thus enhancing the visual acuity of the eye. In particular, the depth of field increases, and presbyopic eyes improve their near vision, for example the ability to read, as a result.

Part of the background to the present invention can be found in the following considerations.

With the aid of "ultrashort" laser pulses, it is possible to produce disruptive processes inside the eye without opening without opening the eye surgically. The interaction mechanism of "photodisruption" is based on "nonlinear absorption." Tissue or material that is originally transparent becomes absorbent above a certain laser intensity threshold. The absorbed light energy results in locally confined microscopic explosions in the focus of the laser beam. Pulses are referred to as "ultrashort" when their duration is less than one picosecond ($10^{-12}$ s).

Such disruption processes are known per se, for example, from applications such as refractive corneal surgery, in which the laser pulses make incisions in the cornea in order to produce tissue flaps or to remove tissue. In particular, it is also known that ultrashort laser pulses near to or just below the disruption threshold have a photochemical effect on tissue and change the optical refractive index. Such mechanisms have also been used to correct refractive errors of the eye.

In these described cases, the cornea of the eye is supposed to remain optically clear after the laser procedure. In a few individual cases, a scar may form in the cornea postoperatively, resulting in optical scattering phenomena. However, this is undesirable and efforts are made to prevent such situations.

Using ultrashort pulses to fragment the greying lens and/or to open the lens capsule is known from cataract surgery.

Using ultrashort pulse to treat age-related long-sightedness (presbyopia) is also known, the ultrashort pulses cutting the lens material that has become hard with age and thus restoring the flexibility and deformability of the lens so that the lens can deform again during the accommodation process. Here, too, the aim is to administer the laser pulses in such doses that the lens remains optically clear after lasering, in order to prevent undesired dazzle.

It is known from EP 2 231 084 B1 that the laser parameters can be so designed that incident light is diffracted or dispersed at the lesions which are produced by the laser pulses and which are left behind in the lens. If a large number of such lesions are produced, it is possible by applying the principle of diffractive optics to create image-forming properties within the lens. These imaging properties can be used to correct visual defects in the eye.

In all the aforementioned applications of photodisruption to the eye, the area irradiated by the laser remains either clear and without any optical effect, or it contributes to imaging by changes in refractive power (refractive) or by scattering (diffractive). In cataract surgery, the parts of the lens fragmented by the laser are removed operatively.

It has been realised in the context of the present invention that, when the laser parameters are skilfully chosen, the lesions produced by the laser can be placed close enough to each other to make the area processed by the laser non-transparent, i.e., to use it as an aperture. If the laser beam is programmed accordingly, pinholes can be created in the natural lens of the eye.

This laser-generated aperture (pinhole) can be used to block the marginal rays of the incident light by applying the principle of the stenopeic gap (pinhole effect). The marginal rays of an optical system are subject to major imaging errors (aberrations). Masking these marginal rays serves to improve the imaging quality of the eye and in particular to increase the depth of field of the eye. When the depth of field is increased, one is able to see objects near and far in sharp focus, even with a non-accommodating (presbyopic) eye.

In one advantageous embodiment of one aspect of the invention, the aperture has laser-induced lesions in different planes in the axial direction. In other words, the control unit is designed to make the laser unit place the laser-induced lesions at different depths (along the visual axis of the eye).

In general, specifications such as "axial" and "lateral" relate to the visual axis of the eye in which the aperture is generated. "Axial" thus denotes a direction along the visual axis, whereas "lateral" denotes a direction perpendicular to the axis of vision.

Suppressing the transmission of light through the aperture region as completely as possible can be better achieved if the aperture extends in the axial direction over more than a single layer of lesions. The aperture can be formed by a plurality of layers with lesions, the layers being laterally offset from one another, for example, by fractions of a periodicity of the lateral distribution of the lesions, particularly when the lesions are distributed more or less regularly inside each of them. However, axially distributing the lesions, in the form of layers or the like, is not necessary, and the lesions may also be arranged irregularly in this respect, for example, randomly, or semi-randomly at least. In extreme cases, each separate lesion can be assigned its own plane.

In another advantageous embodiment of one aspect of the invention, the control unit is designed to control the laser unit with which laser-induced lesions are sequentially created in such a way that they are spaced apart from each other in the lateral and/or axial direction by at least a predetermined distance.

When the laser-induced lesion is introduced, the lens of the eye is locally disturbed. In particular, a blister results in the region of the lesion, which closes again in the course of time, and it is advantageous for the precision and effectiveness of the laser irradiation if the path of light does not pass through a lesion or through the blister which has not yet recovered.

In another advantageous embodiment of one aspect of the invention, the control unit is designed to control the laser unit in a way which results in a random or semi-random distribution of the laser-induced lesions within the aperture region.

The laser-induced lesions may be distributed as closely as possible in each case (under the simplified assumption of a spherical blister that occurs when a respective lesion is created, and with the additional condition that the respective centres of the blisters are offset by the diameter of the blisters, this would be the closest possible sphere packing with a hexagonal arrangement of the lesions). However, this results the arrangement of lesions having a regularity that may lead to undesirable optical effects in certain circumstances. If, at the price of a reduced closeness of lesions, such regularity is broken by randomly distributing the respective positions of the lesions, or by creating the lesions with a sufficiently irregular distribution (i.e., semi-randomly) by controlling it accordingly, such optical effects can be prevented.

In another advantageous embodiment of one aspect of the invention, the device includes an alignment unit for aligning and/or fixating the eye and a light stimulation unit for light stimulation of the eye in order to narrow the pupil, wherein the control unit is designed to control the laser unit on the basis of the narrowed pupil in order to produce marks defining the aperture opening in the lateral and/or axial direction.

In yet another advantageous embodiment of one aspect of the invention, the control unit is designed to control the laser unit for creating the aperture in such a way that light transmission through the lens aperture region is reduced to 20% or less.

It has been found that complete suppression of transmission is not necessary to achieve a sufficient improvement in visual acuity, and that it is sufficient to reduce light transmission to a remainder of 20% or less. Even if greater suppression of transmission is advantageous per se and may be desirable in itself, the effort involved may be too great in the specific case to be justified by the additional benefit.

In another advantageous embodiment of one aspect of the invention, the device comprises the laser unit for creating the aperture in the lens of the eye, wherein the laser unit has a pulsed laser for emitting laser pulses, a focusing unit for focusing the laser pulses, and an alignment unit for aligning the laser pulses.

The laser unit is not necessarily integrated with the control unit in a single device, which means the control unit and the laser unit may also be provided separately so that they do not cooperate with each other until the aperture is actually generated.

In a preferred variant of the above embodiment, the pulsed laser is configured to emit laser pulses having a pulse duration in the range between 10,000 to 10 fs, preferably in the range between 800 and 100 fs, particularly preferably in the range between 350 and 150 fs, with a pulse energy in the range between 100 and 0.01 µJ, preferably in the range between 10 and 0.1 µJ, particularly preferably in the range between 2 and 0.1 µJ, in the wavelength range between 400 and 1,400 nm, preferably in the range between 600 and 1,200 nm, particularly preferably in the range between 800 and 1,100 nm and with a repetition rate in the range between 1 and 100,000 kHz, preferably in the range between 10 and 10,000 kHz, particularly preferably in the range between 100 and 500 kHz, especially preferably with a pulse duration of 150 fs, a pulse energy of 1 µJ, a wavelength in the range between 700 and 1100 nm and a repetition rate of 200 kHz.

According to the teaching of EP 2 231 084 B1, laser pulses with a pulse duration of 100 fs, a pulse energy of 1 µJ, a wavelength of 700 to 1100 nm and a repetition rate of 100 kHz are typical for creating a permanent lesion in the natural lens of the eye. However, in contrast to the approach according to the teaching of EP 2 231084 B1, the object of the present invention is not to create singular diffraction events at the laser lesions spaced defined amounts apart, which events, in sum, cause imaging on transmission through the eye lens. According to the invention, rather, as little light as possible is to be transmitted towards the retina in the region of the created laser lesions, and there is preferably no transmission towards the retina.

According to another aspect of the invention, a computer program is provided, said computer program comprising programming means which cause a device according to the invention to perform a method of creating an aperture in an eye when the computer program is executed on the device. The computer program may be provided, stored, and/or sold on a suitable storage medium, for example, an optical storage medium or a non-volatile electronic storage medium. It may also be provided in conjunction with or as part of a hardware component. The computer program may also be provided in other ways, such as via the Internet or by wired or wireless means of telecommunication.

Features of advantageous embodiments of the invention are defined in the dependent claims, in particular, and a person skilled in the art can also find other advantageous features, embodiments and variants of the invention in the above description and the discussion below.

BRIEF DESCRIPTION OF THE DRAWINGS

In the following, the present invention shall be illustrated and described with reference to the embodiments shown in the Figures, in which.

DETAILED DESCRIPTION OF THE EMBODIMENTS

In the enclosed drawings and in the associated descriptions of said drawings, corresponding or related elements are given corresponding or similar reference signs, where expedient, even when they are to be found in different embodiments.

Figure 1A:
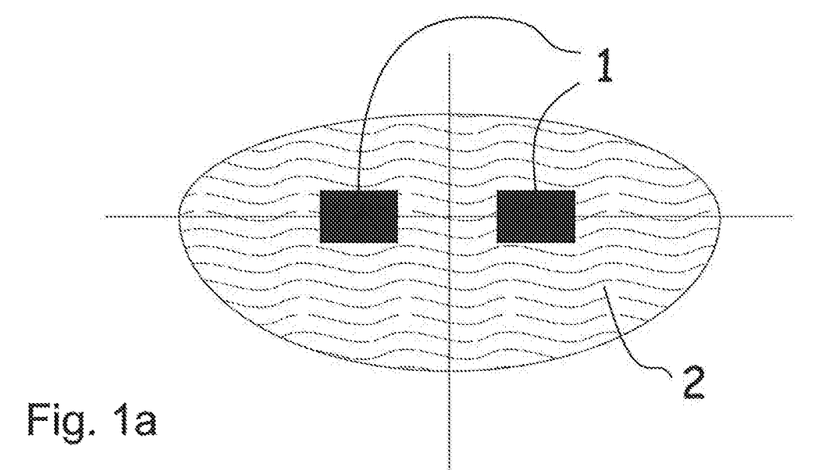
FIGS. 1a-b show schematic views of an aperture in a natural lens of the eye.
Figure 1B:
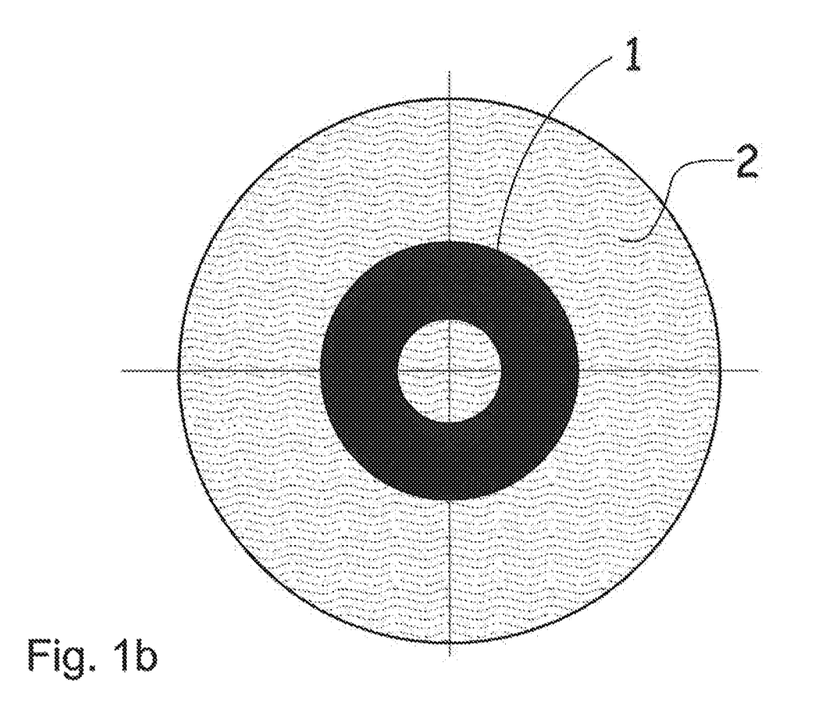

FIG. 1a shows, by way of example, a side view of a laser-generated aperture 1 positioned within a natural lens 2 of an eye, with FIG. 1b showing a corresponding top view of the laser generated aperture 1 positioned within a natural lens 2 of the eye. In this Figure, the axis of vision and the axial direction is drawn as a perpendicular line, and a lateral direction as a horizontal line.

Figure 2:
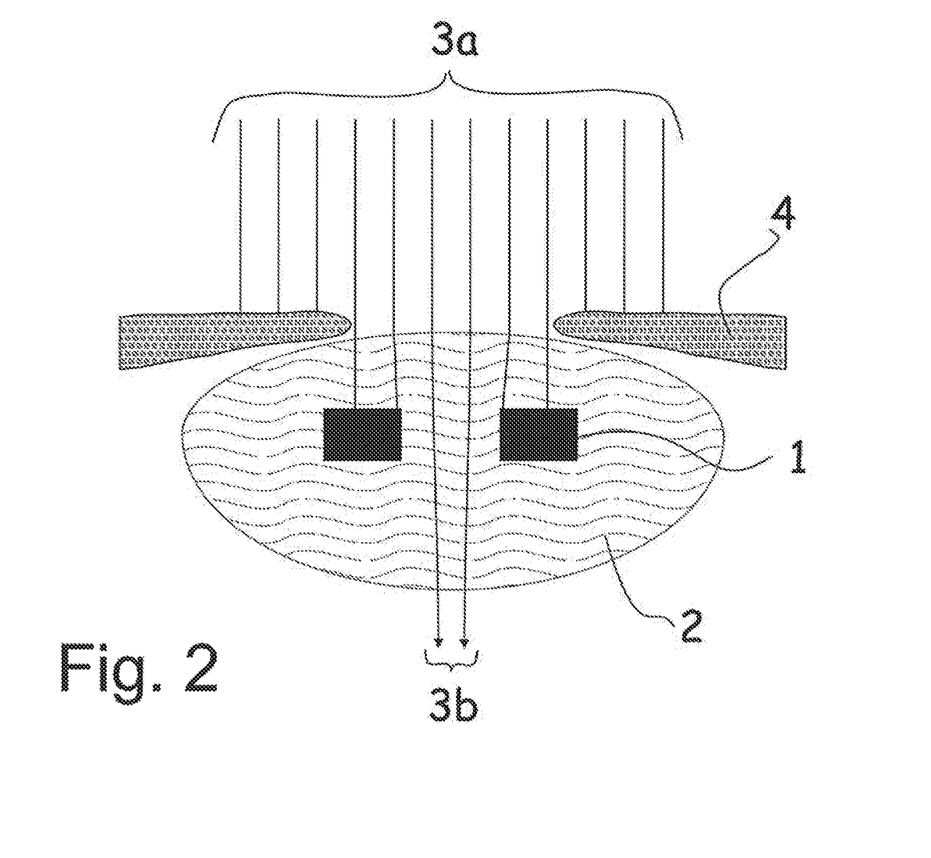
FIG. 2 shows a schematic view for describing the behaviour of light in a lens with the aperture and the iris of the eye.

FIG. 2 shows a schematic view for describing the behaviour of light in a lens with the aperture and the iris of the eye.

Light 3a entering the eye is blocked naturally by the iris 4 of the eye and also by the laser-generated aperture 1 inside lens 2. Only the central part 3b of the light 3a is allowed to pass through to the retina.

Figure 3A:
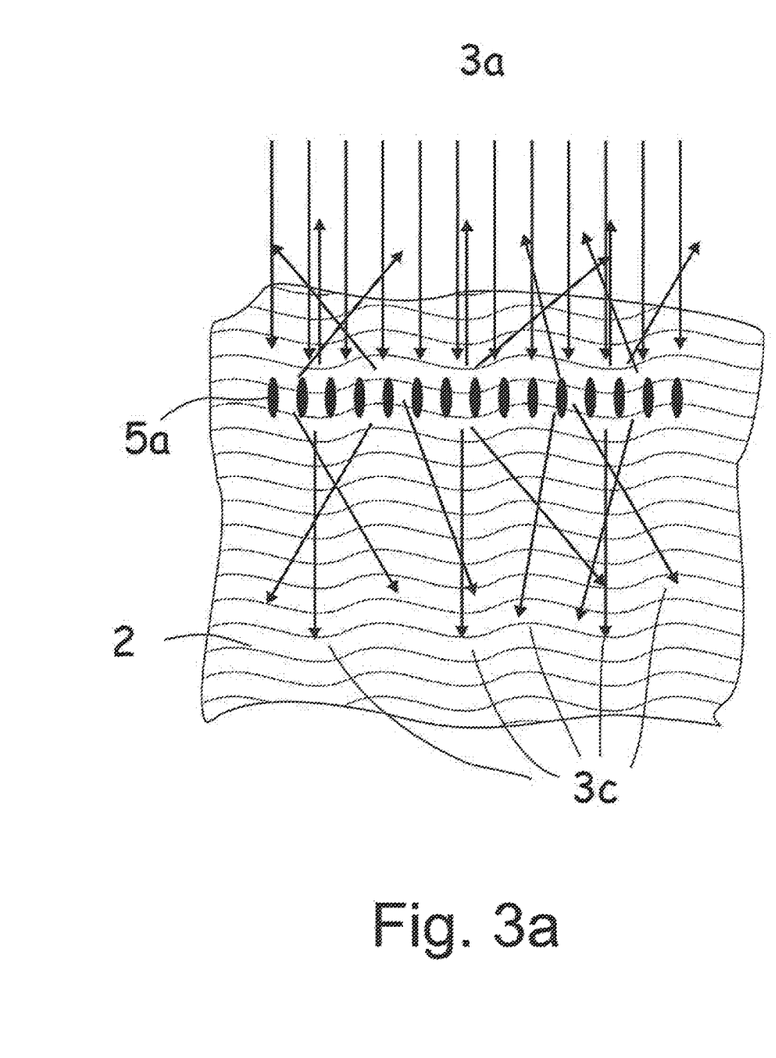
FIGS. 3a-b show schematic views for comparing transmission with a single-layer arrangement of lesions and with a multi-layered arrangement of lesions.
Figure 3B:
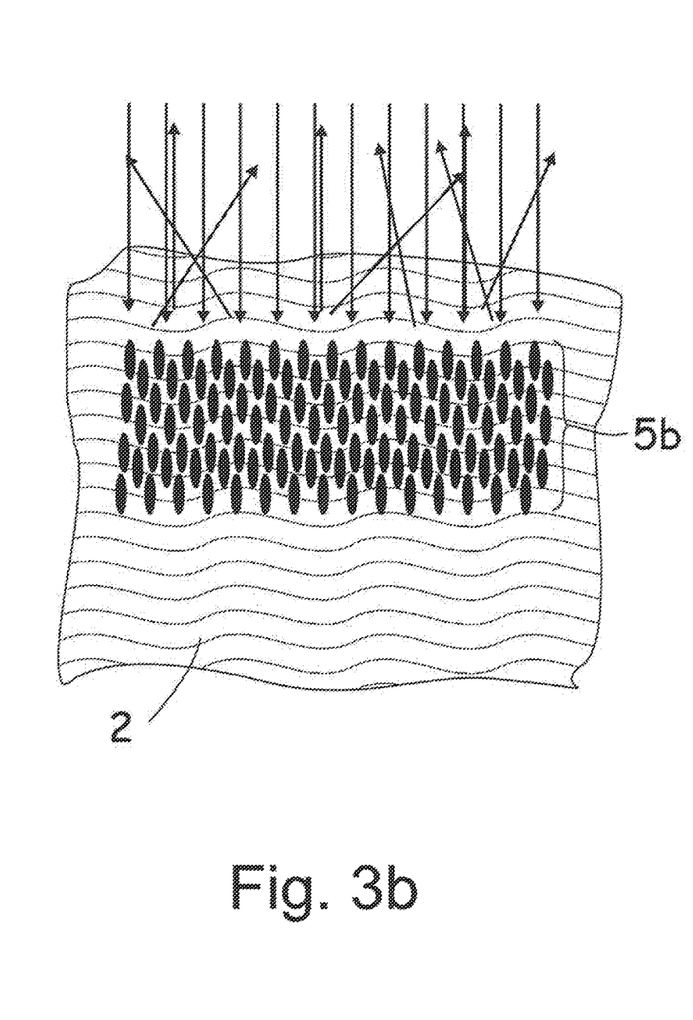

FIGS. 3a-b show schematic views for comparing transmission with a single-layer arrangement of lesions and with a multi-layered arrangement of lesions, respectively. A single-layer arrangement of laser lesions 5a within the lens 2 of the eye may, as in this example, result in incident light 3a mainly being scattered in all directions. Even when the lateral arrangement of lesions 5a is very dense, what is still a substantial proportion of the incident light may be scattered forwards (3c) and may thus reach the retina. In contrast, a plurality of layers of laterally closely-packed lesions 5b, as illustrated in FIG. 3b, will reduce the likelihood of photons being scattered in the direction of the retina.

If, as envisaged by the present invention, as little light as possible is to pass through the aperture region (surrounding the aperture opening), the laser lesions must be arranged as close as possible laterally. As some of the laser lesions do not absorb the light, but merely scatter it, some of the incident light may nevertheless scatter forwards and thus reach the retina, even when the lesions are arranged laterally very close together (FIG. 3a). The scattered photons that reach the retina do not contribute to image formation and are perceived as annoying. Contrast vision, in particular, is adversely affected as a result.

If, on the other hand, a plurality of layers of laterally closely packed lesions are also created in the axial direction, then the likelihood of photons being scattered towards the retina becomes increasingly smaller. Once there is a certain thickness or quantity of successive layers, the amount of transmitted light is so small, even without any further special measures regarding the design of the lesions, that the contrast is reduced to only an insignificant or acceptable extent during image formation on the retina (FIG. 3b).

Figure 4A:
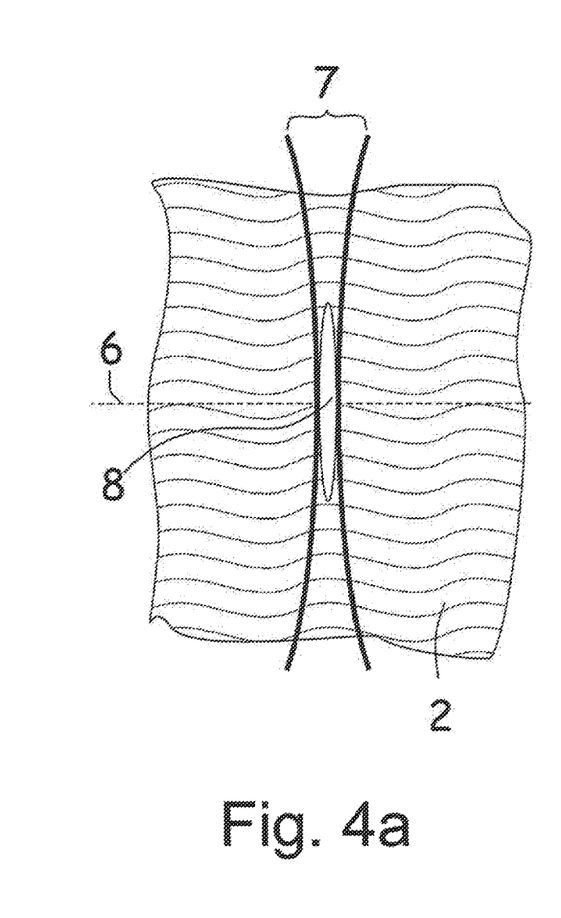
FIGS. 4a-c shows schematic illustrations of the processes occurring during photodisruption.
Figure 4B:
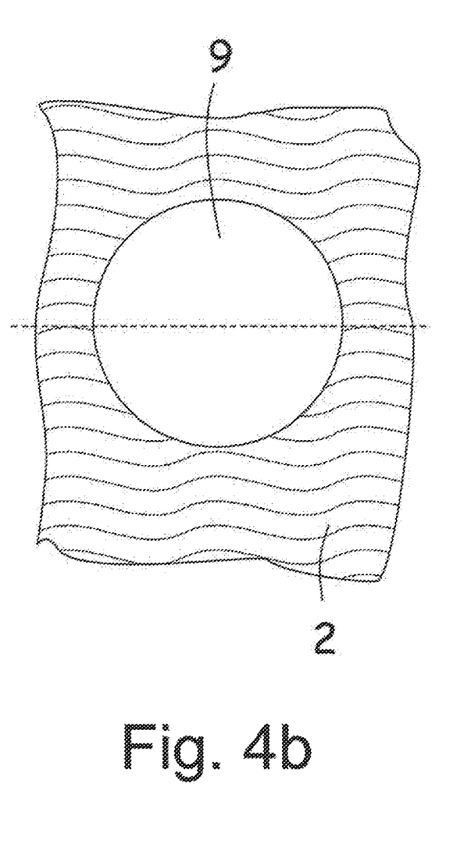
Figure 4C:
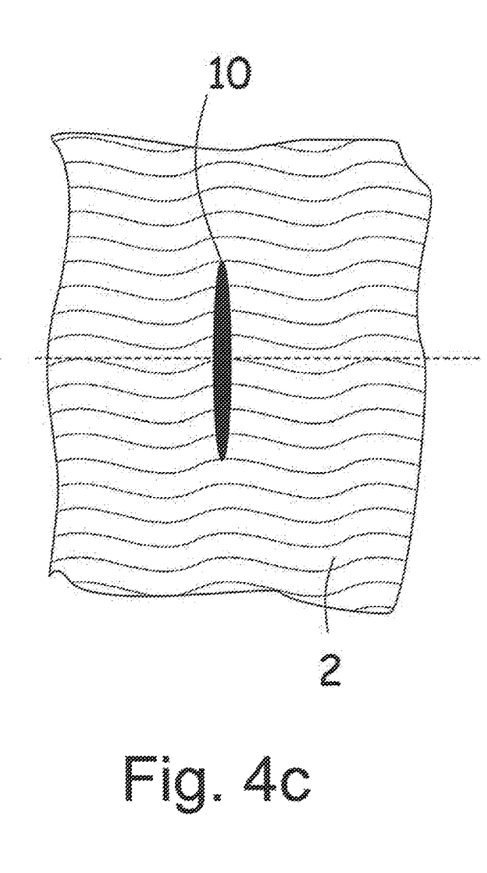

FIG. 4a-c show schematic illustrations of the processes occurring during photodisruption.

FIG. 4a illustrates photodisruption occurring in the focal plane 6 of the incident laser beam 7 when the laser beam is of sufficient intensity. Due to physical factors, interaction zone 8 typically has a prolate shape.

FIG. 4b illustrates that, immediately after disruption by the evaporating lens material, a gas bubble 9 is produced with a substantially greater dilation than the interaction zone 8 of the laser light.

After a certain amount of time (milliseconds to hours), depending on the size of the gas bubble, the gas has diffused into the surroundings of the lens tissue and the gas bubble has collapsed, as shown in FIG. 4c. What remains is modified lens tissue of prolate shape (referred to here as a "laser lesion" 10). Laser lesion 10 is characterised by strongly scattering and absorbing properties for visible light.

Figure 5A:
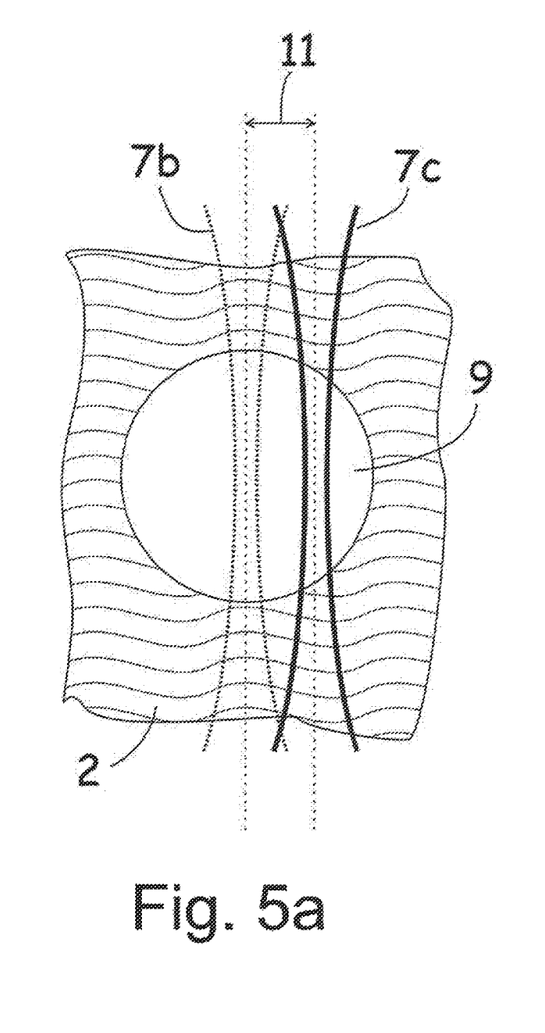
FIGS. 5a-b show schematic illustrations in a case where laser pulses are positioned too close together.
Figure 5B:
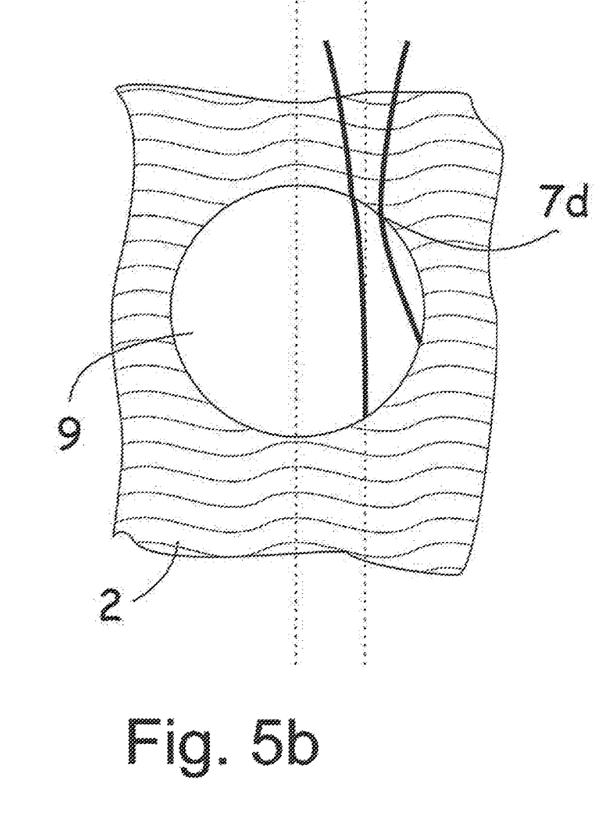

FIG. 5a-b show schematic illustrations in a case where laser pulses are positioned too close together, If two sequential laser pulses 7b, 7c are spaced apart by a distance 11 that is smaller than the diameter of the remaining gas bubble 9, the subsequent pulse 7c is directed into gas bubble 9, as shown in FIG. 5a. If the laser pulse hits the gas bubble 9 inside lens 2, the light of laser pulse 7d is deflected due to the refraction differentials between the lens material and the gas bubble, as illustrated in FIG. 5b.

The laser parameters are preferably set so that the threshold for photodisruption is exceeded in the focal plane of the laser pulse so as to produce a permanent lesion (FIG. 4a). However, this results in a small gas bubble being produced at the focus of the laser pulse immediately after exposure to the laser (FIG. 4b). The gas is the product of the water vaporised by the laser pulse or of components of the lens that transition into the gas phase. Due to the viscosity and the chemical solubility in the tissue water of the gases and vapours produced, it takes a certain amount of time until the bubble has completely collapsed, leaving behind a typically elliptical, prolate lesion that permanently scatters or absorbs the incident light (FIG. 4c). The amount of time required for the gas bubble to collapse is usually much longer (milliseconds to hours) than the time interval between two laser pulses (nanoseconds to milliseconds). If the laser is controlled so that a subsequent pulse is placed a distance apart that is less than the diameter of the residual gas bubble, the subsequent pulse is directed into the gas bubble (FIG. 5a). In this situation, the light of the laser pulse is deflected due to the refraction differentials between the lens material and the gas bubble (FIG. 5b). The focusing quality of the laser pulse may be destroyed in the process, with the result that the light intensity at the focus can no longer be maintained sufficiently to exceed the threshold for a photodisruption process. Depending on the size of the gas bubble and the temporal and spatial distance between the laser pulses, it is possible for a plurality of sequential pulses to be deflected at a gas bubble and not produce any photodisruption. The result is that patterns of lesions are produced that are spaced much further apart than the patterns of laser foci that were originally intended. The masking effect of the entire laser area is less efficient as a consequence.

This reduction in efficiency can be circumvented by programming the laser control such that sequential laser pulses are spaced further apart than the diameter of the gas bubbles at the moment in time that the subsequent pulse arrives.

The gaps that remain between the laser lesions can be closed in a second and/or in multiple sequences of laser pulses once the gas bubbles have collapsed.

If the gas bubbles take longer to collapse than scanning the entire surface of a plane of laser lesions, the laser can be programmed to create another layer of laser lesions in a further direction facing the laser source. The laser lesions are then placed preferably at the gaps left behind by the laser lesions in the plane before. This process can be repeated several times, thus creating a solid body that allows sufficiently little light to reach the retina, once a certain number of layers of laser lesions has been created.

In another embodiment, the laser lesions can be randomly spaced apart on average. This irregular spatial distribution prevents the laser lesions from forming an optical grating and thus cause undesirable diffraction effects.

If the laser-generated aperture is created by multiple layers of laser lesions, the aperture is a spatial object. In addition to centring the aperture, for example in relation to the visual axis of the eye, it is not only the lateral orientation of the aperture that is important, therefore, but also its orientation. If its orientation is skewed, the circular aperture acts in projection to the visual axis or to the incident light as an ellipse. Furthermore, the light will produce strong scattering phenomena at the edges of the opening and cause dazzle.

For that reason, it is advantageous to keep the axial extension of the aperture (in the direction of the beam) as small as possible, but nevertheless superimpose as many layers of laser lesions as possible.

Figure 6A:
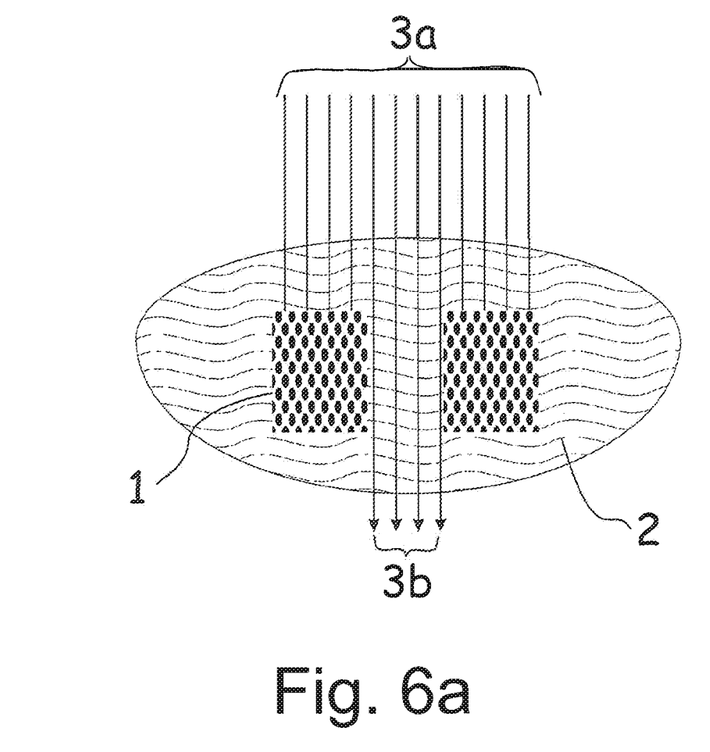
FIG. 6a-b show schematic views for orientation of the aperture in relation to the optical axis.

FIG. 6a illustrates that when aperture 1 in lens 2 is correctly oriented parallel to the optical axis or to incident light 3a, the central beams of the pencil of beams 3a are let through, and the marginal rays are blocked by scattering or absorption.

Figure 6B:
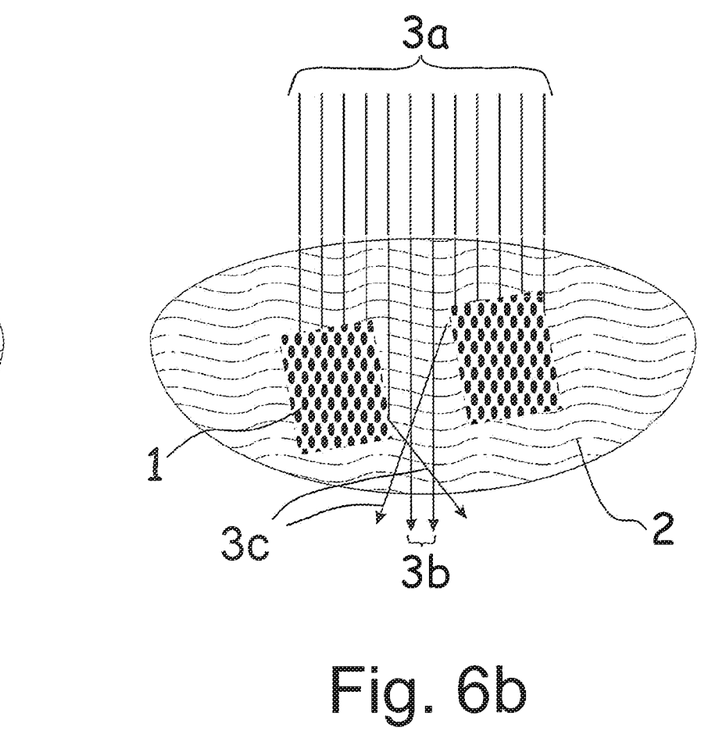

FIG. 6b illustrates that when the orientation of the aperture is skewed, the incident light 3a causes scattering phenomena at the edges of the aperture. Light beams 3c, which will hit the edges of the aperture, are only slightly scattered and can reach the retina, where they cause undesirable dazzle as a result.

Figure 7A:
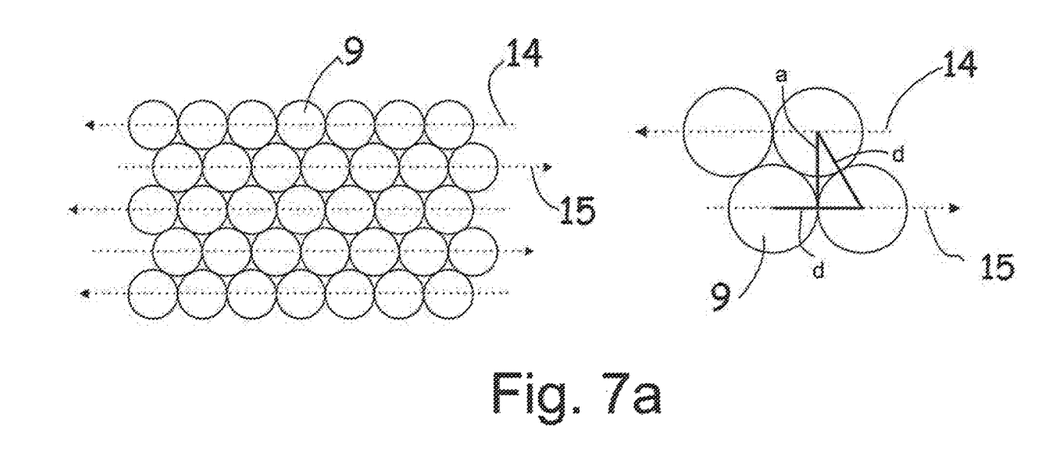
FIGS. 7a-c show schematic views of an axial arrangement of laser-induced lesions.
Figure 7B:
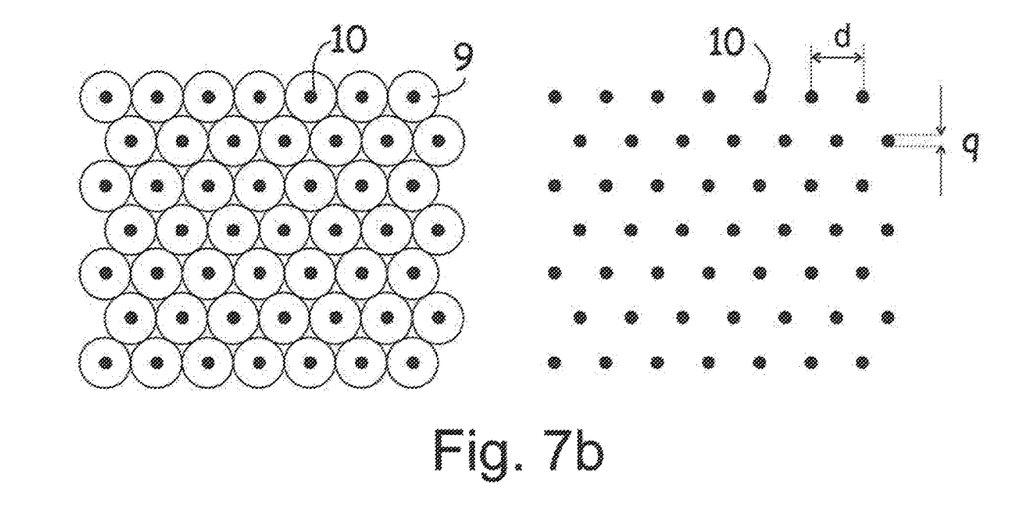
Figure 7C:
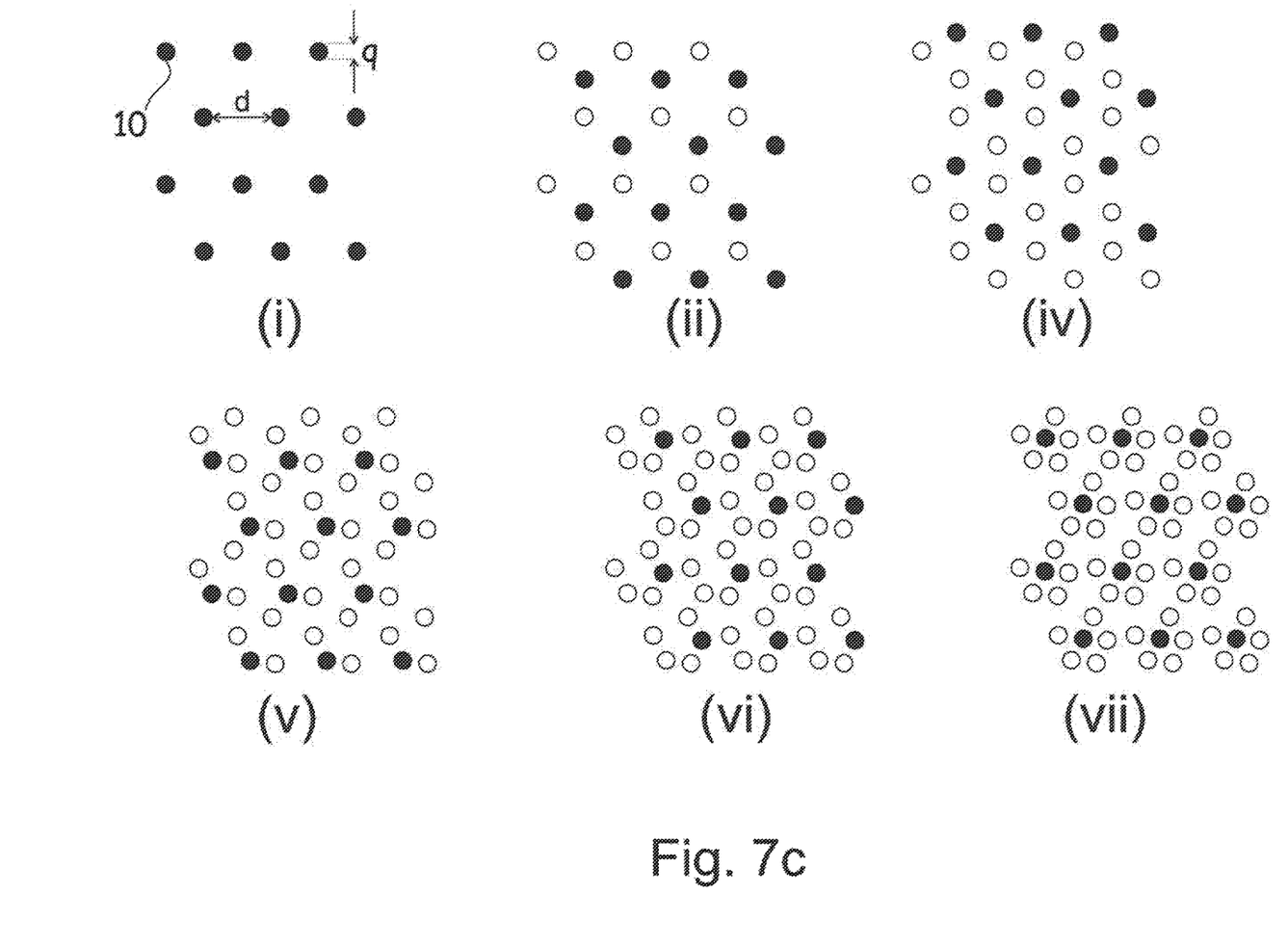

FIG. 7a-c show schematic views of an axial arrangement of laser-induced lesions.

An arrangement of laser lesions that is as closely packed as possible is obtained by spacing the laser pulses as far apart in one direction as the maximum expansion of a laser-generated gas bubble in the lens tissue. The result is a chain of single gas bubbles that touch each other, but preferably do not merge with each other. (FIG. 7a). In an adjacent path 15, parallel to the first path 14, the individual laser pulses are arranged offset from each other by around half the maximum diameter d of the gas bubbles. The minimum spacing a between the adjacent paths is calculated as $$a = \sqrt{3/4} \times d$$

Once a plane has been completely scanned, the result is a carpet of lesions 10 separated from each other by a distance d. Lesions 10, and thus the effective circular area for absorbing or scattering incident light 3a, have a diameter of q. Therefore, such a plane of laser lesions can scatter or scatter only a fraction $(q/d)^2$ of the incident light (FIG. 7b).

A second plane of laser lesions can now be created here. This plane lies in the direction facing the laser beam and is spaced a distance a from the previous plane. A smaller distance can also be chosen if the gas bubbles in the plane decreased in size during creation of a plane of lesions. The raster pattern of laser pulses may be offset in its lateral orientation in such a way that the lesions created by the laser pulses in the newer layer are between the lesions of the previous layer. In a subsequent, third layer, at a distance a or less from the second layer, a grid of lesions can again be created. In this case, the laser foci and the resultant lesions are placed into the projection of the remaining gaps between all the previous lesions. The sequence of creating the individual layers of lesions in axially different planes is shown by way of example in FIG. 7c for the first six layers. Solid black circles were used for the currently created lesions and open white circles for the respective previous layers.

This sequence can be repeated until a sufficient number of lesions covering the entire surface of the aperture has been created in total. For example, if 100% of the aperture area is to be covered with lesions, then at least $(d/q)^2$ layers of laser lesions need to be created.

FIG. 8a-d show schematic views for describing procedures for creating an aperture according to the invention with previous marking.

Figure 8A:
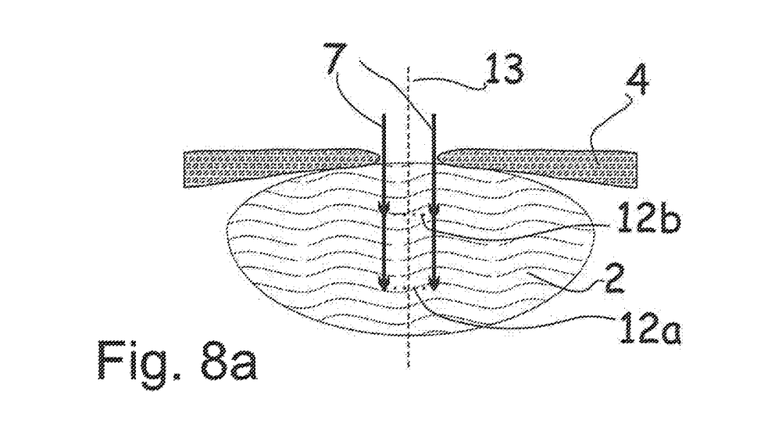
FIGS. 8a-d show schematic views for describing procedures for creating an aperture according to the invention with previous marking.
Figure 8B:
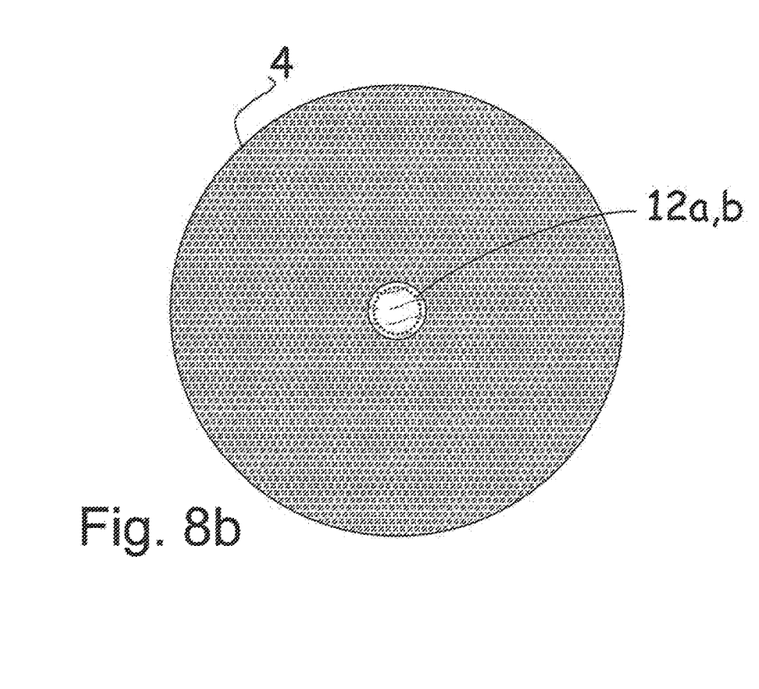

One or more orientation points 12a, 12b, as shown in FIG. 8a, can be lasered into lens 2 with the aid of laser beam 7 while the pupil is narrow (miosis). These can be two rings, for example, indicating the posterior (12a) and anterior position (12b) of the aperture opening. The lateral position of the marks is limited by the inner edge of the iris 4. FIG. 8b shows the same situation as in FIG. 8a from the operator perspective (top view)

Figure 8C:
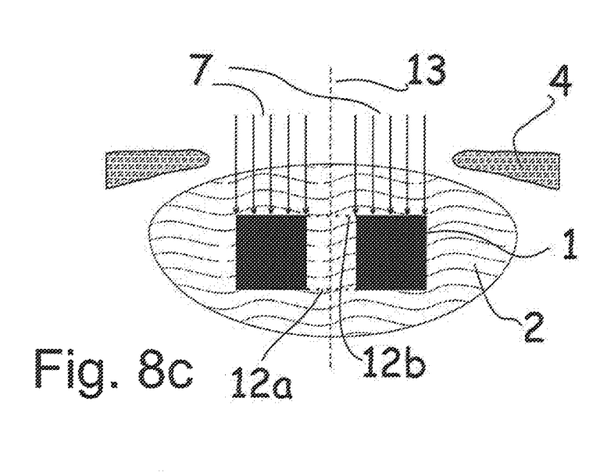
Figure 8D:
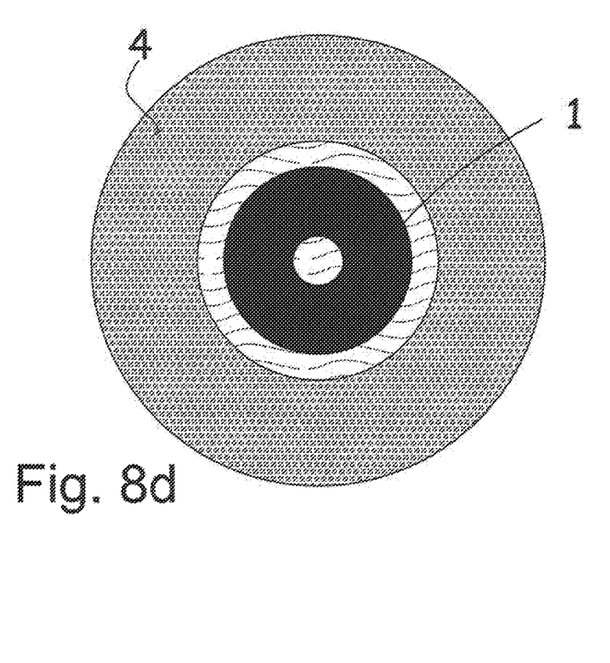

FIG. 8c shows how, when the pupils are dilated (mydriasis), the entire aperture 1 can be lasered into lens 2 without the iris 4 blocking the beam path of laser 7. The previously placed marks 12a, 12b help to centre the aperture accordingly and to orient it along the visual axis 13. FIG. 8d shows the same situation as in FIG. 8c from the operator perspective (top view).

The laser-generated aperture can be centred and oriented in relation to the visual axis of the eye. It is advantageous, for example, to position the centre of the aperture in the middle between the centre of the pupil and the "first Purkinje reflection." If the pupil needs to be dilated by medication during laser application (mydriasis), it is advantageous if a mark is first applied to the surface of the cornea, for example with dye, when the pupil is narrowed.

Advantageous positioning results from centring and orientation at the iris 4 when the pupil is narrow (miosis). After the patient's eye has been aligned with the laser apparatus and fixated, if necessary, for example by means of a commonly used "patient interface," the eye is stimulated by comparatively bright light. The eye consequently adapts by narrowing the pupil (miosis). In this situation, one or more orientation points 12a, 12b can be lasered into lens 2 by laser 7, for example two rings indicating the posterior and anterior position of the aperture opening (FIGS. 8a, 8b). Positioning can be supported by standard imaging techniques such as optical coherence tomography (OCT).

Once the marks have been placed, the light stimulus is removed. The eye, or both the patient's eyes, are preferably left in maximum darkness. The eye will consequently adapt once again to the light conditions and will dilate the pupil (mydriasis). In this situation, the entire aperture 1 be lasered into lens 2 without the iris 4 blocking the beam path of the laser. The previously placed marks 12a, 12b help to centre the aperture accordingly and to orient it along the visual axis 13. If natural mydriasis is not sufficient to move the iris 4 completely out of the beam path of laser 7, further mydriasis can be induced by medication. The advantage of this approach is that, after the laser procedure, in bright daylight, the naturally narrowed, adapted pupil matches the opening of the laser-generated aperture.

Even if different aspects or features of the invention are shown in combination in the Figures, it is clear to a person skilled in the art, unless otherwise specified, that the combinations shown and discussed are not the only ones possible. More particularly, it is possible to swap corresponding units or groups of features from different embodiments.

In implementations of the invention, individual components, such as a processor, may wholly or partly assume the functions of various elements mentioned in the claims. Procedures or processes such as controls, calculations, measurements, or similar may be implemented as programming means of a computer program and/or as special hardware components.

The invention claimed is:

1. A device for creating an aperture in an eye, said device comprising:
   a control unit for a laser unit;
   the control unit being adapted to control the laser unit to create the aperture in a lens of the eye, wherein the aperture is used to increase the depth of field of the eye and is formed by laser-induced lesions which reduce light transmission through a lens aperture region surrounding an aperture opening;
   an alignment unit for aligning and/or fixating the eye; and
   a light stimulation unit for light stimulation of the eye in order to narrow the pupil;
   wherein the control unit is adapted to control the laser unit on the basis of the pupil in a dilated state in order to produce marks within the lens of the eye outward of the opening in a lateral direction and/or an axial direction relative the visual access of the eye; and wherein the control unit is adapted to control the laser unit with which laser-induced lesions are sequentially created in such a way that they are spaced apart from each other in the lateral direction and/or an axial direction relative to a visual axis of the eye by at least a predetermined distance in a first plane, wherein sequential laser pulses for creating the laser-induced lesions are spaced further apart than a diameter of gas bubbles at the moment in time that the subsequent pulse arrives, and wherein the control unit is further adapted to control the laser unit such that gaps that remain between the laser-induced lesions can be closed in a following sequence of laser pulses in a second plane axially offset from the first plane once the gas bubbles have collapsed.

2. The device according to claim 1, wherein the aperture has laser-induced lesions in different planes in an axial direction relative a visual axis of the eye.

3. The device according to claim 1, wherein the control unit is adapted to control the laser unit in such a way that results in a random or semi-random distribution of the laser-induced lesions within the lens aperture region.

4. The device according to claim 1, wherein the control unit is adapted to control the laser unit for creating the aperture in such a way that light transmission through the lens aperture region is reduced to 20% or less.

5. The device according to claim 1, further comprising a laser unit for creating the aperture in the lens of the eye, wherein the laser unit comprises a pulsed laser for emitting laser pulses, a focusing unit for focusing the laser pulses, and an alignment unit for aligning the laser pulses.

6. The device according to claim 5, wherein the pulsed laser is configured to emit laser pulses having:
 a pulse duration in the range between 10,000 to 10 fs;
 a pulse energy in the range between 100 and 0.01 µJ;
 a wavelength range between 400 and 1,400 nm; and
 a repetition rate in the range between 1 and 100,000 kHz.

7. The device according to claim 5, wherein the pulsed laser is configured to emit laser pulses having:
 a pulse duration in the range between 800 and 100 fs;
 a pulse energy in the range between 10 and 0.1 µl;
 a wavelength range between 600 and 1,200 nm; and
 a repetition rate in the range between 10 and 10,000 kHz.

8. The device according to claim 5, wherein the pulsed laser is configured to emit laser pulses having:
 a pulse duration in the range between 350 and 150 fs;
 a pulse energy in the range between 2 and 0.1 µJ;
 a wavelength range between 800 and 1,100 nm; and
 a repetition rate in the range between 100 and 500 kHz.

9. The device according to claim 5, wherein the pulsed laser is configured to emit laser pulses having:
 a pulse duration of 150 fs;
 a pulse energy of 1 µJ;
 a wavelength in the range between 700 and 1100 nm; and
 a repetition rate of 200 kHz.

10. A method of generating control commands for a laser unit for creating an aperture in an eye, wherein the control commands cause the laser unit to create the aperture in a lens of the eye, and wherein the aperture is used to increase the depth of field of the eye and is formed by laser-induced lesions which reduce light transmission through a lens aperture region surrounding an aperture opening;
 an alignment unit for aligning and/or fixating the eye; and
 a light stimulation unit for light stimulation of the eye in order to narrow the pupil;

wherein the control unit is adapted to control the laser unit on the basis of the narrowed pupil in order to produce marks within the lens of the eye, the marks defining the aperture opening in a lateral direction and/or an axial direction relative to a visual axis of the eye;

wherein the control unit is adapted to control the laser unit on the basis of the pupil in a dilated state in order to produce marks within the lens of the eye outward of the opening in a lateral direction and/or an axial direction relative the visual access of the eye; and wherein the control unit is adapted to control the laser unit with which laser-induced lesions are sequentially created in such a way that they are spaced apart from each other in a lateral direction and/or an axial direction relative a visual axis of the eye by at least a predetermined distance in a first plane, wherein sequential laser pulses for creating the laser-induced lesions are spaced further apart than a diameter of gas bubbles at the moment in time that the subsequent pulse arrives, wherein the control unit is further adapted to control the laser unit such that gaps that remain between the laser-induced lesions can be closed in a following sequence of laser pulses in a second plane axially offset from the first plane once the gas bubbles have collapsed.

11. The method of generating control commands for a laser unit for creating an aperture in an eye of claim 10, wherein the laser unit comprises a pulsed laser for emitting laser pulses, a focusing unit for focusing the laser pulses, and an alignment unit for aligning the laser pulses.

12. The method for generating control commands for a laser unit for creating an aperture in an eye of claim 11, wherein the pulsed laser is configured to emit laser pulses having:
 a pulse duration in the range between 10,000 to 10 fs;
 a pulse energy in the range between 100 and 0.01 µJ;
 a wavelength range between 400 and 1,400 nm; and
 a repetition rate in the range between 1 and 100,000 kHz.

13. A method of creating an aperture in an eye, said method comprising the step of:
 controlling a laser unit to create the aperture in a lens of the eye, wherein the aperture is used to increase the depth of field of the eye and is formed by laser-induced lesions which reduce light transmission through a lens aperture region surrounding an aperture opening; wherein:
 the control unit is adapted to control the laser unit with which laser-induced lesions are sequentially created in such a way that they are spaced apart from each other in a lateral direction and/or an axial direction relative a visual axis of the eye by at least a predetermined distance in a first plane, wherein sequential laser pulses for creating the laser-induced lesions are spaced further apart than a diameter of gas bubbles at the moment in time that the subsequent pulse arrives, wherein the control unit is further adapted to control the laser unit such that gaps that remain between the laser-induced lesions can be closed in a following sequence of laser pulses in a second plane axially offset from the first plane once the gas bubbles have collapsed, and/or
 providing:
 an alignment unit for aligning and/or fixating the eye; and
 a light stimulation unit for light stimulation of the eye in order to narrow the pupil;
 wherein the control unit is adapted to control the laser unit on the basis of the narrowed pupil in order to produce marks within the lens of the eye, the marks defining the aperture opening in a lateral direction and/or an axial direction relative to a visual axis of the eye and the marks within the lens of the eye extending outward of the aperture opening in a lateral direction and/or an axial direction relative to the visual access of the eye.

14. The method of creating an aperture in an eye of claim 13, wherein the laser unit comprises a pulsed laser for emitting laser pulses, a focusing unit for focusing the laser pulses, and an alignment unit for aligning the laser pulses.

15. The method of creating an aperture in an eye of claim 14, wherein the pulsed laser is configured to emit laser pulses having:
   a pulse duration in the range between 10,000 to 10 fs;
   a pulse energy in the range between 100 and 0.01 µJ;
   a wavelength range between 400 and 1,400 nm; and
   a repetition rate in the range between 1 and 100,000 kHz.

16. A computer program for a device for creating an aperture in an eye comprising:
   a control unit for a laser unit operated in accordance with the computer program;
   the control unit being adapted to control the laser unit to create the aperture in a lens of the eye when the computer program is executed on the device, wherein the aperture is used to increase the depth of field of the eye and is formed by laser-induced lesions which reduce light transmission through a lens aperture region surrounding an aperture opening;
   an alignment unit for aligning and/or fixating the eye; and
   a light stimulation unit for light stimulation of the eye in order to narrow the pupil;
   wherein the control unit is adapted to control the laser unit on the basis of the narrowed pupil in order to produce marks within the lens of the eye, the marks defining the aperture opening in a lateral direction and/or an axial direction relative to a visual axis of the eye;
   wherein the control unit is adapted to control the laser unit on the basis of the narrowed pupil in order to produce marks within the lens of the eye, the marks defining the aperture opening in a lateral direction and/or an axial direction relative to a visual axis of the eye; and
   wherein the control unit is adapted to control the laser unit on the basis of the pupil in a dilated state in order to produce marks within the lens of the eye outward of the opening in a lateral direction and/or an axial direction relative the visual access of the eye; and
   wherein the control unit is adapted to control the laser unit with which laser-induced lesions are sequentially created in such a way that they are spaced apart from each other in a lateral direction and/or an axial direction relative a visual axis of the eye by at least a predetermined distance in a first plane, wherein sequential laser pulses for creating the laser-induced lesions are spaced further apart than a diameter of gas bubbles at the moment in time that the subsequent pulse arrives, wherein the control unit is further adapted to control the laser unit such that gaps that remain between the laser-induced lesions can be closed in a following sequence of laser pulses in a second plane axially offset from the first plane once the gas bubbles have collapsed.

17. The computer program for a device for creating an aperture in an eye of claim 16, wherein the laser unit comprises a pulsed laser for emitting laser pulses, a focusing unit for focusing the laser pulses, and an alignment unit for aligning the laser pulses.

18. The computer program for a device for creating an aperture in an eye of claim 17, wherein the pulsed laser is configured to emit laser pulses having:
   a pulse duration in the range between 10,000 to 10 fs;
   a pulse energy in the range between 100 and 0.01 µJ;
   a wavelength range between 400 and 1,400 nm; and
   a repetition rate in the range between 1 and 100,000 kHz.

19. A device for creating an aperture in an eye, said device comprising:
   a control unit for a laser unit;
   the control unit being adapted to control the laser unit to create the aperture in a lens of the eye, wherein the aperture is used to increase the depth of field of the eye and is formed by laser-induced lesions which reduce light transmission through a lens aperture region surrounding an aperture opening;
   an alignment unit for aligning and/or fixating the eye; and
   a light stimulation unit for light stimulation of the eye in order to narrow the pupil;
   wherein the control unit is adapted to control the laser unit on the basis of the narrowed pupil in order to produce marks within the lens of the eye, the marks defining the aperture opening in a lateral direction and/or an axial direction relative to a visual axis of the eye;
   wherein the control unit is adapted to control the laser unit on the basis of the pupil in a dilated state in order to produce marks within the lens of the eye outward of the opening in a lateral direction and/or an axial direction relative to the visual access of the eye; and
   wherein the marks are produced in a plurality of axially arranged planes, such that the marks in a first plane are laterally and/or axially laterally offset from the marks produced in an adjacent plane.

20. A device for creating an aperture in an eye, said device comprising:
   a control unit for a laser unit;
   the control unit being adapted to control the laser unit to create the aperture in a lens of the eye, wherein the aperture is used to increase the depth of field of the eye and is formed by laser-induced lesions which reduce light transmission through a lens aperture region surrounding an aperture opening, the region being defined by the pupil in a narrowed state and the pupil in a dilated state;
   wherein the control unit is adapted to control the laser unit with which laser-induced lesions are sequentially created in such a way that they are spaced apart from each other in the lateral direction and/or an axial direction relative a visual axis of the eye by at least a predetermined distance in a first plane, wherein sequential laser pulses for creating the laser-induced lesions are spaced further apart than a diameter of gas bubbles at the moment in time that the subsequent pulse arrives, and wherein the control unit is further adapted to control the laser unit such that gaps that remain between the laser-induced lesions can be closed in a following sequence of laser pulses in a second plane axially offset from the first plane once the gas bubbles have collapsed.

* * * * *

UNITED STATES PATENT AND TRADEMARK OFFICE
CERTIFICATE OF CORRECTION

| | | |
|---|---|---|
| PATENT NO. | : 11,406,535 B2 | Page 1 of 1 |
| APPLICATION NO. | : 16/760694 | |
| DATED | : August 9, 2022 | |
| INVENTOR(S) | : Lubatschowski | |

It is certified that error appears in the above-identified patent and that said Letters Patent is hereby corrected as shown below:

In the Specification

Column 9, Line 51, "(d/q)" should be --(q/d)--;

In the Claims

Column 10, Claim 1, Line 65, insert --wherein the control unit is adapted to control the laser unit on the basis of the narrowed pupil in order to produce marks within the lens of the eye, the marks defining the aperture opening in a lateral direction and/or an axial direction relative a visual axis of the eye;--;

Column 11, Claim 9, Line 56, "1100" should be --1,100--;

Column 12, Claim 10, Line 10, "access" should be --axis--;

Column 13, Claim 13, Line 5, "access" should be --axis--;

Column 13, Claim 16, Line 42, "the pupil" should be --the narrowed pupil--;

Column 13, Claim 16, Line 45, "access" should be --axis--;

Column 14, Claim 19, Line 29, "the pupil" should be --the narrowed pupil--; and

Column 14, Claim 19, Line 32, "access" should be --axis--.

Signed and Sealed this
Twenty-second Day of August, 2023

Katherine Kelly Vidal
*Director of the United States Patent and Trademark Office*